United States Patent [19]
Carballada et al.

[11] Patent Number: 5,653,969
[45] Date of Patent: Aug. 5, 1997

[54] LOW RESIDUE HAIR CARE COMPOSITIONS

[75] Inventors: Jose Antonio Carballada; Lauren Ann Thaman, both of Cincinnati; Sanjeev Midha, Blue Ash, all of Ohio

[73] Assignee: The Procter & Gamble Company, Cincinnati, Ohio

[21] Appl. No.: 621,738

[22] Filed: Mar. 21, 1996

[51] Int. Cl.$^6$ .................................................... A61K 7/48
[52] U.S. Cl. ............................ 424/70.16; 424/70.12; 424/70.11
[58] Field of Search .......................... 424/70.12, 70.11, 424/70.16

[56] References Cited

U.S. PATENT DOCUMENTS

| | | | |
|---|---|---|---|
| 3,208,911 | 9/1965 | Oppliger | 167/87 |
| 3,957,970 | 5/1976 | Korkis | 424/70 |
| 4,030,512 | 6/1977 | Papantoniou et al. | 132/7 |
| 4,136,250 | 1/1979 | Mueller et al. | 528/29 |
| 4,185,087 | 1/1980 | Morlino | 424/70 |
| 4,277,595 | 7/1981 | Deichert et al. | 528/26 |
| 4,479,893 | 10/1984 | Hirota et al. | 252/542 |
| 4,563,347 | 1/1986 | Starch | 424/70 |
| 4,601,902 | 7/1986 | Fridd et al. | 424/70 |
| 4,654,161 | 3/1987 | Kollmeier et al. | 252/174.15 |
| 4,659,777 | 4/1987 | Riffle et al. | 525/100 |
| 4,663,413 | 5/1987 | Ward et al. | 528/26 |
| 4,689,383 | 8/1987 | Riffle et al. | 528/12 |
| 4,693,935 | 9/1987 | Mazurek | 428/352 |
| 4,724,851 | 2/1988 | Cornwall et al. | 132/7 |
| 4,728,571 | 3/1988 | Clemens et al. | 428/352 |
| 4,733,677 | 3/1988 | Gee et al. | 132/7 |
| 4,744,978 | 5/1988 | Homan et al. | 424/70 |
| 4,814,402 | 3/1989 | Nakashima et al. | 526/245 |
| 4,902,499 | 2/1990 | Bolich, Jr. et al. | 424/70 |
| 4,963,595 | 10/1990 | Ward et al. | 525/415 |
| 4,972,037 | 11/1990 | Garbe et al. | 526/245 |
| 4,981,902 | 1/1991 | Mitra et al. | 524/547 |
| 4,981,903 | 1/1991 | Garbe et al. | 524/547 |
| 4,988,506 | 1/1991 | Mitra et al. | 424/81 |
| 5,021,477 | 6/1991 | Garbe et al. | 424/70 |
| 5,061,481 | 10/1991 | Suzuki et al. | 424/63 |
| 5,100,658 | 3/1992 | Bolich, Jr. et al. | 424/70 |
| 5,104,646 | 4/1992 | Bolich, Jr. et al. | 424/70 |
| 5,106,609 | 4/1992 | Bolich, Jr. et al. | 424/70 |
| 5,166,276 | 11/1992 | Hayama et al. | 525/329 |
| 5,219,560 | 6/1993 | Suzuki et al. | 424/63 |
| 5,229,435 | 7/1993 | Sakai et al. | 523/105 |

FOREIGN PATENT DOCUMENTS

| | | | |
|---|---|---|---|
| 0 117 360 | 12/1983 | European Pat. Off. | A61K 7/06 |
| 0 408 311 A2 | 7/1990 | European Pat. Off. | C08F 230/08 |
| 5 6092-811 | 7/1981 | Japan | A61K 7/11 |
| 5 6129-300 | 10/1981 | Japan | A61K 7/06 |
| 4-359912 | 6/1991 | Japan | C08F 299/08 |
| 4-359913 | 6/1991 | Japan | C08F 299/08 |
| 4-360812 | 6/1991 | Japan | A61K 7/00 |
| WO88/05060 | 7/1988 | WIPO | C08F 30/08 |

*Primary Examiner*—Margaret W. Glass
*Attorney, Agent, or Firm*—Anthony D. Sabatelli; David K. Dabbiere

[57] ABSTRACT

The present invention relates to rinse-off hair care compositions that leave a low residue on the hair after repeated use. These compositions have good hair style retention properties and have a natural, non-sticky feel upon the hair. These compositions comprise a hydrophobic copolymer component and a carrier suitable for application to the hair. The copolymer component further comprises a hydrophobic copolymer and a volatile hydrophobic solvent.

17 Claims, No Drawings

LOW RESIDUE HAIR CARE COMPOSITIONS

TECHNICAL FIELD

The present invention relates to rinse-off hair care compositions having a low residue on the hair. These compositions have good hair style retention properties and have a natural, non-sticky feel upon the hair. These compositions comprise a hydrophobic copolymer component and a carrier suitable for application to the hair. The copolymer component further comprises a hydrophobic copolymer and a volatile, hydrophobic solvent.

BACKGROUND OF THE INVENTION

The desire to have hair retain a particular style is widely held. Style retention is generally accomplished by application of either permanent chemical alteration products or temporary styling products. A permanent chemical alteration product, which is commonly referred to as a "hair perm," typically involves treating the hair with various sulfur-containing compounds in order to break the disulfie bends in the hair fibers, thereby enabling one to alter the shape and orientation of the hair fibers. However, hair perm products have the disadvantage of being harsh and damaging to the hair, and of being long-lasting and difficult to reverse. Conversely, temporary styling products generally do not break the chemical bends in the hair fibers. These temporary styling products typically are in the form of gels, lotions, mousses, or sprays containing polymeric resins or gums for coating the hair fibers and bending them together. Many temporary styling products are inconvenient to use and have the disadvantage of not allowing one to readily restyle the hair after the initial application and styling is completed, without further application of additional product. It would be preferable to deliver styling and hold benefits from rinse-off products such as conditioners and shampoos. These types of rinse-off products, however, require styling agents that are substantive to the hair and not readily removed during the rinsing process. Especially useful styling and hold agents for rinse-off compositions are hydrophobic polymeric materials. Such hydrophobic materials, however, may cause a buildup of an unsightly visible residue on the hair with repeated usage. This residue can eventually completely surround the hair shaft and can be difficult to remove with normal shampooing. Therefore, the need exists for improved rinse-off compositions for providing temporary styling and hold of human hair without the residue and negatives often associated with such compositions.

It has surprisingly been found in the present invention that rinse-off hair care compositions comprising certain hydrophobic copolymers provide excellent temporary hair hold and style retention benefits with very low visible residue buildup on the hair. These compositions can be made in any of the conventional rinse-off forms including, but not limited to, shampoos, conditioners, mousses, gels, lotions, sprays, and the like. The compositions of the present invention provide the benefits without leaving the hair feeling stiff or sticky. Hair to which the compositions of the present invention have been applied can be restyled several times without requiring reapplication of the compositions.

Hair care compositions containing various copolymers are well-known in the prior art. However, none of these references either teach or suggest compositions having a low visible residue on the hair. See for example, U.S. Pat. No. 3,208,911, to Oppliger, issued Sept. 28, 1965, U.S. Pat. No. 4,601,902, to Fridd et at, issued Jul. 22, 1986, U.S. Pat. No. 4,654,161, to Kollmeier et at., issued Mar. 31, 1987, U.S. Pat. No. 5,106,609, to Bolich hr. et al., issued Apr. 21, 1992, U.S. Pat. No. 4,693,935, to Mazurek, issued Sept. 15, 1987, European Patent Application No. 412,704, to Bolich et at., published Feb. 2, 1991.

The compositions of the present invention comprise a hydrophobic copolymer component and a carrier suitable for application to the hair, wherein the hydrophobic copolymer component further comprises a hydrophobic copolymer and a volatile, hydrophobic solvent.

It is therefore an object of the present invention to provide rinse-off compositions which are useful for styling and holding the hair.

It is another object of the present invention to provide compositions which are useful for providing a temporary hold and styling benefit for hair.

It is another object of the present invention to provide compositions which do not leave a visible residue on the hair.

It is another object of the present invention to provide methods for styling and holding the hair.

These and other objects will become readily apparent from the detailed description which follows.

SUMMARY OF THE INVENTION

The present invention relates to a rinse-off hair care composition comprising:
  (a) from about 0.25% to about 70% of a copolymer component, comprising:
    (i) from about 1.5% to about 70% by weight of said copolymer component, of a hydrophobic copolymer having a weight average molecular weight from about 10,000 to about 5,000,000, said copolymer comprising a polymeric backbone and hydrophobic polymeric side chains grafted to said backbone, wherein the weight percent of said copolymer in said rinse-off hair care composition is from about 0.10% to about 7%; and
    (ii) from about 30% to about 98.5% of a volatile hydrophobic solvent having a boiling point at 1 atmosphere of about 225° C. or less; and
  (b) from about 30% to about 99.75% of a carrier suitable for application to human hair,
wherein said rinse-off hair care composition has a residue index on human hair of about 20 or greater.

In further embodiments, the present invention relates to methods for styling and holding the hair utilizing these hair care compositions.

Unless otherwise indicated, all percentages and ratios used herein are by weight of the total composition. All weight percentages, unless otherwise indicated, are on an actives weight basis. All measurements made are at 25° C., unless otherwise designated. The invention hereof can comprise, consist of, or consist essentially of, the essential as well as optional ingredients and components described herein.

DETAILED DESCRIPTION OF THE INVENTION

The compositions of the present invention comprise a hydrophobic copolymer component and a carrier suitable for application to the hair, wherein the hydrophobic copolymer component further comprises a hydrophobic copolymer and a volatile, hydrophobic solvent.

The hydrophobic copolymers of the present invention can be described as graft copolymers. The term "graft copolymers" is familiar to one of ordinary skill in polymer science and is used herein to describe the copolymers which result by adding or "grafting" a polymeric chemical moiety (i.e. "grafts") onto another polymeric moiety commonly referred to as the "backbone". The backbone typically has a higher molecular weight than the grafts. Thus, graft copolymers can be described as polymers having pendant polymeric side chains, and as being formed from the "grafting" or incorporation of polymeric side chains onto or into a polymer. The polymer to which the grafts are incorporated can be homopolymers or copolymers. The graft copolymers are derived from a variety of monomer units.

The copolymers of the present invention can be prepared from the copolymerization of monomer units and macromonomer units such that the macromonomer units are "grafted" or incorporated into the resulting copolymer. The term "macromonomer" is a term familiar to one of ordinary skill in polymer science, and is used to described a polymeric material containing a polymerizable moiety. In other words, a macromonomer is a macromolecular monomer, which is essentially a high molecular weight type of monomer building block unit which can be used in a polymerization reaction to form polymers with itself, with other monomers, or with other macromonomers.

The term "hydrophobic" is used herein consistent with its standard meaning of lacking affinity for water, whereas "hydrophilic" is used herein consistent with its standard meaning of having affinity for water. As used herein in relation to monomer units and polymeric materials, including the macromonomers, copolymers, and solvents for the copolymers, "hydrophobic" means sustantially water insoluble. In this regard, "substantially water insoluble" shall refer to a material that is not soluble in distilled (or equivalent) water, at 25° C., at a concentration of 0.2% by weight, and preferably not soluble at 0.1% by weight. In contrast, "hydrophilic" means substantially water soluble. "Substantially water soluble" shall refer to a material that is soluble in distilled (or equivalent) water, at 25° C., at a concentration of 0.2% by weight, and are preferably soluble at 1.0% by weight.

The term "rinse-off", as contrasted with the term "leave-on", is used herein to mean that the compositions of the present invention are used in a context whereby the composition is ultimately rinsed or washed from the hair either after or during the application of the product. A "leave-on" product, refers to a hair care composition that is applied to the hair and not further subjected to a rinsing step. Nonlimiting examples of rinse-off products of the present invention include hair conditioners and shampoos.

The term "suitable for application to human hair" as used herein, means that the compositions or components thereof so described are suitable for use in contact with human hair and the the scalp and skin without undue toxicity, incompatibility, instability, allergic response, and the like.

The aforementioned definitions shall also apply to other materials so described herein, to the extent any other definitions regarding such materials are consistent with those stated above.

The compositions of the present invention comprise the following essential components.

Copolymer Component

The rinse-off hair care compositions of the present invention comprise from about 0.25% to about 70%, preferably from about 4% to about 30%, and more preferably from about 8% to about 18%, by weight, based on the weight of the rinse-off hair care composition, of a copolymer component. The copolymer component further comprises a hydrophobic copolymer and a volatile hydrophobic solvent for the hydrophobic copolymer.

Hydrophobic Copolymer

The copolymer component of the present invention comprises from about 1.5% to about 70%, preferably from about 5% to about 40%, and more preferably from about 10% to about 25%, by weight, based on the weight of the copolymer component, of a hydrophobic copolymer. Based on the weight of the overall rinse-off hair care composition, the hydrophobic copolymer comprises from about 0.1% to about 7%, preferably from about 1% to about 4%, and more preferably from about 1.5% to about 2.5%, by weight.

The copolymers of the present invention have a weight average molecular weight, in grams/mole, of at least about 10,000. There is no upper limit for molecular weight except that which limits applicability of the invention for practical reasons, such as viscosity, processing, aesthetic characteristics, formulation compatibility, etc. The weight average molecular weight is generally less than about 5,000,000, more generally less than about 2,5000,000, and typically less than about 1,500,000. Preferably, the weight average molecular weight is from about 10,000 to about 5,000,000, more preferably from about 75,000 to about 2,000,000, even more preferably from about 100,000 to about 15000,000, and most preferably from about 125,000 to about 1,000,000.

The copolymers of the present invention are formed from the copolymerization of randomly repeating A monomer units and B macromonomer units, preferably wherein the A monomer units are selected from at least one polymerizable, ethylenically unsaturated monomer unit; and the B macromonomer units are selected from at least one hydrophobic macromonomer unit which contains a polymeric portion and a moiety copolymerizable with the A monomer units, preferably an ethylenically unsaturated moiety which is copolymerizable with the A monomer units. In preferred embodiments of these copolymers, the backbone is formed from the polymerization of the A monomer units with the ethylenically unsaturated portion of the hydrophobic B macromonomer units. The polymeric portion of the B macromonomer units forms the hydrophobic side chains of the copolymer. The A monomer units and B macromonomer units can be selected form a wide variety of structures as long as the copolymer has the required properties and molecular weight described herein.

The copolymers are prepared by the polymerization combination of A monomers and B macromonomers and can be characterized by the weight percent of the monomers and macromonomers charged to the reaction vessel in which the polymerization reaction is run.

The A monomer units and the hydrophobic B macromonomer units comprise or are derived from hydrophobic monomers and optionally a limited amount of hydrophilic monomers. The particular relative amounts of hydrophilic and hydrophobic monomers can vary as long as the graft copolymer as a whole is soluble in the volatile, hydrophobic solvent hereof. Solubility of the graft copolymer material, or component thereof, in the volatile, hydrophobic solvents hereof is determined according to whether such material remains in solution or precipitates out of solution at 25° C. Graft copolymers that are soluble in the volatile, hydrophobic solvents of the present invention typically comprise from about 0% to about 5%, by weight of the optional hydrophilic monomer units.

As will be clear to one skilled in the art and especially from the Examples, the copolymer may have one or more hydrophobic side chains grafted to the backbone. In addition, the compositions of the present invention may include, in addition to the copolymer, corresponding copolymers having no hydrophobic side chains grafted to the backbone. As known in the art, synthetic graft copolymerization processes may produce a mixture of polymer molecules containing no, one, or more than one hydrophobic side chains covalently bonded to and pendant from the polymeric backbone. From knowledge of the amount and number average molecular weight of hydrophobic side chains in a polymer sample, and the number average molecular weight of the polymer sample, it is possible to calculate the average number of hydrophobic side chains per polymer backbone.

The copolymer component of the present invention, when dried to a film having 0.05% or less of the volatile hydrophobic solvent, have a Tg or Tm of at least about −20° C., more preferably at least about 25° C., so that the copolymers are not unduly sticky, or "tacky" to the touch. As used herein, the abbreviation "Tg" refers to the glass transition temperature of the backbone of the polymer, and the abbreviation "Tm" refers to the crystalline melting point of the backbone, if such a transition exists for a given polymer. Preferably, both the Tg and the Tm, if any, are above about −20° C., more preferably above about 25° C.

The graftedcopolymers should satisfy the following three criteria:
  (1) when dried the copolymer phase-separates into a discontinuous phase which includes the grafted polymeric side chain portion and a continuous phase which includes the non-side chain portion;
  (2) the polymeric side chain portion is covalently bonded to the backbone portion; and
  (3) the number average molecular weight of the polymeric side chain portion is from about 5,000 to about 50,000.

Without being limited by theory, it is believed that the phase separation property provides a specific orientation of the copolymer which results in the desired combination of tactile feel, film-forming or adhesive benefits, and the ability to dry quickly and completely. The phase-separating nature of the compositions of the present invention may be determined as follows.

The copolymer is cast as a solid film out of a solvent (i.e., the volatile, hydrophobic solvent of the present invention, which dissolves both the backbone and the side chain graft portions). This film is then sectioned and examined by transmission electron microscopy. Microphase separation is demonstrated by the observation of inclusions in the continuous phase. These inclusions should have the proper size to match the size of the side chains (typically a few hundred nm or less) and the proper density to match the amount of side chain present. This behavior is well documented in the literature for polymers with this structure (see, for example, S. D. Smith, Ph. D. Thesis, University of Virginia, 1987, and references cited therein.

The copolymers of the present invention are prepared by the polymerization combination of A monomers and B macromonomers. The copolymers can be synthesized by free radical polymerization of the monomers and macromonomers. The general principles of free radical polymerization methods are well understood. See, for example, Odian, "Principles of Polymerization", 3rd edition, John Wiley & Sons, 1991, pp. 198–334. The desired A monomers and B macromonomers are all placed in a reactor, along with a sufficient amount of a mutual solvent so that when the reaction is complete the viscosity of the reaction is reasonable. Undesired terminators, especially oxygen, are removed as needed. This is done by evacuation or by purging with an inert gas, such as argon or nitrogen. The initiator is introduced and the reaction brought to the temperature needed for initiation to occur, assuming thermal initiators are used. Alternatively, redox or radiation initiation can be used. The polymerization is allowed to proceed as long as needed for a high level of conversion to be achieved, typically from a few hours to a few days. The solvent is then removed, usually by evaporation or by precipitating the copolymer by addition of a nonsolvent. The copolymer can be further purified, as desired.

As an alternative to a batch reaction, the copolymer can be made by a semi-continuous or continuous process. In the semi-continuous process, two or more additions of monomers or macromonomers are made during the polymerization reaction. This is advantageous when the copolymer is made of several monomers which react during the polymerization at different rates. The proportions of monomers added to the reaction at the separate points of addition can be adjusted by one of ordinary skill in the art such that the polymers of the final product have a more uniform structure. In other words, the polymers of the final product will have a more consistent monomer content distribution for each of the monomer types charged to the reaction.

Examples of related copolymers and how they are made are described in detail in U.S. Pat. No. 4,693,935, Mazurek, issued Sep. 15, 1987, U.S. Pat. No. 4,728,571, Clemens et al., issued Mar. 1, 1988, both of which are incorporated herein by reference. Additional silicone grafted polymers are also disclosed in U.S. Pat. No. 5,480,634, Hayama et al., issued Oct. 2, 1996, U.S. Pat. No. 5,166,276, Hayama et al., issued Nov. 24, 1992, U.S. Pat. No. 5,061,481, issued Oct. 29, 1991, Suzuki et al., U.S. Pat. No. 5,106,609, Bolich et al., issued Apr. 21, 1992, U.S. Pat. No. 5,100,658, Bolich et al., issued Mar. 31, 1992, U.S. Pat. No. 5,100,657, Ansher-Jackson, et al., issued Mar. 31, 1992, U.S. Pat. No. 5,104, 646, Bolich et al., issued Apr. 14, 1992 all of which are incorporated by reference herein in their entirety.

The particular relative amounts of A monomers and B macromonomers can vary as long as the copolymer backbone is soluble in the volatile, hydrophobic solvent hereof and the silicone grafted copolymer exhibits phase separation when dried.

The copolymers are prepared by the polymerization combination of A monomers and B macromonomers. The copolymer composition is characterized by the amount of each monomer charged to the polymerization reaction vessel, or alternatively used in a continuous or semi-continuous process.

By appropriate selection and combination of the particular A monomer units and B macromonomer units, and by the choice of specific relative ratios of the units well within the ability of one of ordinary skill in the art, the copolymers can be optimized for various physical properties and for compatibility with other ingredients commonly used in hair care applications.

A Monomer Units

The hydrophobic copolymers of the present invention comprise from about 50% to about 85%, preferably from about 60% to about 85%, and more preferably from about 70% to about 80%, by weight of the hydrophobic copolymer, of A monomer units.

The A monomer unit is selected from copolymerizable monomers, preferably ethylenically unsaturated monomers. Either a single type of A monomer unit or combinations of two or more A monomer units can be utilized. The A monomers are selected to meet the requirements of the copolymer. By "copolymerizable", as used herein, is meant that the A monomer can be reacted with or polymerized with the B macromonomers in a polymerization reaction using one or more conventional synthetic techniques, such as ionic, emulsion, dispersion, Ziegler-Natta, free radical, group transfer or step growth polymerization. In the present invention, monomers and macromonmers that are copolymerizable using conventional free radical initiated techniques are preferred. The term "ethyleneically unsaturated" is used herein to mean a material that contains at least one polymerizable carbon-carbon double bond, which can be mono-, di-, tri- or tetra-substituted. The A monomer units include hydrophobic monomer units, and optionally hydrophilic monomer units.

Nonlimiting classes of A hydrophobic monomers useful herein include monomers selected from the group consisting of unsaturated carboxylic acid esters of C1–C18 alcohols, unsaturated alcohols (preferably having about 12 to about 30 carbons), unsaturated hydrocarbons, aromatic hydrocarbons containing unsaturated alkyl groups, vinyl esters of carboxylic acids, vinyl ethers, allyl esters of carboyxlic acids, allyl ethers, and mixtures thereof.

Representative examples of hydrophobic monomers include acrylic or methacrylic acid esters of $C_1$–$C_{18}$ alcohols such as methanol, ethanol, methoxy ethanol, 1-propanol, 1-butanol, 2-methyl-1-propanol, 1-pentanol, 1-decanol, 2-ethylhexanol, cyclohexanol, and the like; dicyclopentenyl acrylate; 4-biphenyl acrylate, pentachlorophenyl acrylate; 3,5-dimethyladamantyl acrylate; 4-methoxycarbonylphenyl methacrylate, trimethylsilyl methacrylate; styrenes such as methyl styrene; t-butyl styrene, isopropyl styrene; vinyl esters, such as vinyl acetate, vinyl neononanoate, vinyl pivalate; and vinyl propionate; vinyl chloride; vinyl toluene; alkyl vinyl ethers, including isobutyl vinyl ether and s-butyl vinyl ether; allyl chloride, allyl acetate, 1,2-butadiene; 1,3-butadiene, 1,3-hexadiene, 1,3-cyclohexadiene; bicycloheptadiene; 2,3-dicarboxylmethyl-1,6-hexadiene; ethylene; propylene; isoprene; 1-butene, 2-butene, isobutylene, indene; norbornylene; β-pinene; α-pinene; and mixtures thereof.

Preferred hydrophobic monomers suitable for use as the A monomer units include monomers selected from the group consisting of n-butyl methacrylate, isobutyl methacrylate, t-butyl acrylate, t-butyl methacrylate, 2-ethylhexyl methacrylate, methyl methacrylate, indene, norbornylene, β-pinene, α-pinene, vinyl pivalate, vinyl neononanoate, dicyclopentenyl acrylate, 4-biphenyl acrylate, pentachlorophenyl acrylate, 3,5-dimethyladamantyl acrylate, 3,5-dimethyladamentyl methacrylate, 4-methoxycarbonylphenyl methacrylate, trimethylsilyl methacrylate, t-butyl styrene and mixtures thereof. More preferred are monomer units selected from the group consisting of t-butyl styrene, t-butyl acrylate, t-butyl methacrylate, and mixtures thereof.

As mentioned above, lower levels of hydrophilic monomers, i.e. from about 0% to about 5% based on the weight of the copolymer, can optionally be present in the copolymers of the present invention. Nonlimiting examples of such monomers include those selected from the group consisting of acrylic acid, methacrylic acid, N,N-dimethylacrylamide, dimethylaminoethyl methacrylate, methacrylamide, N-t-butyl acrylamide, maleic acid, maleic anhydride, crotonic acid, itaconic acid, acrylamide, hydroxyethyl methacrylate, diallyldimethyl ammonium chloride, vinyl pyrrolidone, vinyl pyridine, vinyl imidazole, styrene sulfonate, allyl alcohol, and mixtures thereof. Also useful herein are salts and alkyl quaternized derivatives of such monomers, as applicable.

B Macromonomer Units

The hydrophobic copolymers of the present invention comprise from about 15% to about 50%, preferably from about 15% to about 40%, and more preferably from about 20% to about 30%, by weight of the copolymer of B macromonomer units.

The B macromonomer units are hydrophobic macromonomers copolymerizable with the A monomers, said B macromonomers preferably having an ethylenically unsaturated moiety. Either a single type of B macromonomer unit or combinations or two or more B macromonomer units can be utilized herein. The B macromonomers are selected to meet the requirements of the copolymer. By "copolymerizable", as used herein, is meant that the B macromonomers can be reacted with or polymerized with the A monomers in a polymerization reaction using one or more conventional synthetic techniques, as described above.

B macromonomers that are useful herein contain a polymeric portion and a copolyermizable moiety which is preferably an ethylenically unsaturated moiety. Typically, the preferred B macromonomers are those that are endcapped with the ethylenically unsaturated moiety. By "endcapped" as used herein is meant that the ethylenically unsaturated moiety is at or near a terminal position of the macromonomer.

The B macromonomers can be synthesized utilizing a variety of standard synthetic procedures familiar to the polymer chemist of ordinary skill in the art. Furthermore, these macromonomers can be synthesized starting from commercially available polymers. Typically, the weight average molecular weight of the B macromonomer is from about 5,000 to about 50,000.

Preferably, the B macromonomer units are selected from the group consisting of polysiloxane macromonomers, polyalkylene macromonomers, and mixtures thereof.

Polysiloxane B macromonomers are exemplified by the general formula:

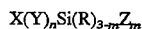

wherein X is an ethylenically unsaturated group copolymerizable with the A monomers, such as a vinyl group; Y is a divalent linking group; R is a hydrogen, hydroxyl, lower alkyl (e.g. $C_1$–$C_4$), aryl, alkaryl, alkoxy, or alkylamino; Z is a monovalent siloxane polymeric moiety having a number average molecular weight of at least about 1500, is essentially unreactive under copolymerization conditions, and is pendant from the vinyl polymeric backbone described above; n is 0 or 1; and m is an integer from 1 to 3. The B macromonomer has a weight average molecular weight from about 5000 to about 50,000, preferably from about 5,000 to about 30,000, more preferably from about 8,000 to about 25,000.

Preferably, the B macromonomer has a formula selected from the following formulas:

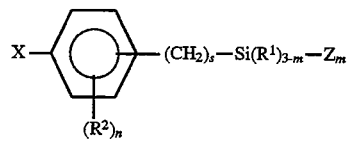

or

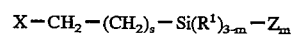

or

-continued

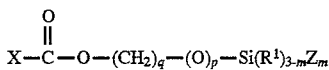

In these structures s is an integer from 0 to about 6, preferably 0, 1, or 2, more preferably 0 or 1; m is an integer from 1 to 3, preferably 1; p is 0 or 1; q is an integer from 2 to 6; $R^2$ is $C_1$–$C_{14}$ alkyl or $C_7$–$C_{10}$ alkylaryl, preferably $C_1$–$C_6$ alkyl or $C_1$–$C_{10}$ alkylaryl, more preferably $C_1$–$C_2$ alkyl; n is an integer from 0 to 4, preferably 0 or 1, more preferably 0; $R^1$ is hydrogen, hydroxyl, lower alkyl, alkoxy, alkylamino, aryl, or alkaryl, preferably $R^1$ is alkyl; X is

$R^3$ is hydrogen or —COOH, preferably $R^3$ is hydrogen; $R^4$ is hydrogen, methyl or —$CH_2COOH$, preferably $R^4$ is methyl; Z is

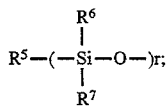

$R^5$, $R^6$, and $R^7$, independently are lower alkyl, alkoxy, alkylamino, aryl, arkaryl, hydrogen or hydroxyl, preferably $R^5$, $R^6$, and $R^7$ are alkyls; and r is an integer of from about 60 to about 700, preferably about 60 to about 400, more preferably r is from about 100 to about 350. Most preferably, $R^5$, $R^6$, and $R^7$ are methyl, p=0, and q=3.

When the B macromonomer molecular weight is less than or equal to about 13,000 and r is less than or equal to about 170, the weight percentage of the B monomer charged to the polymerization reactor is preferably from about 25% to about 40%, more preferably 25% to about 30%. When the B monomer molecular weight is greater than about 13,000 and r is greater than about 170, the weight percentage of the C monomer charged is preferably from about 15% to about 40% more preferably 20% to about 30%.

Polyalkylene macromonomers are exemplified by the general formula:

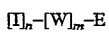

wherein I is an optionally present initiator (i.e. n=0 or 1), W is a hydrophobic monomer unit, E is an endcapping group, and m is an integer from about 10 to about 2000.

I is an optionally present chemical initiator moiety. Without being limited by theory, I can be derived from a chemical initiator or solvent used in the synthesis of the B macromonomer. Nonlimiting examples of such initiators from which I can be derived include hydrogen ion, hydrogen radical, hydride ion, hydroxide ion, hydroxyl radical, peroxide radical, peroxide anion, C1–C20 carbocations, C1–C20 carbanions, C1–C20 carbon radicals, C1–C20 aliphatic and aromatic alkoxy anions, ammonium ion, and substituted ammonium ions (e.g., C1–C20 alkyl and C1–C20 alkoxy substituted), and mixtures thereof. I can be derived from any useful solvent, nonlimiting examples of which include water, methanol, ethanol, propanol, isopropanol, acetone, hexane, dichloromethane, chloroform, benzene, toluene, and mixtures thereof.

W is selected from one or more hydrophobic monomer units. Nonlimiting classes of such monomers include C1–C18 acrylate esters, C1–C18 (alk)acrylate esters, C2–C30 straight and branched chain alkenes, styrenes, C1–C30 vinyl ethers, C4–C30 straight and branched chain dienes, and mixtures thereof.

Nonlimiting examples of W groups include those selected from the group consisting of n-butyl acrylate, dodecyl acrylate, ethyl acrylate, 2-ethybutyl acrylate, n-heptyl acrylate, n-hexylacrylate, iso-butyl acrylate, iso-decyl acrylate, iso-propyl acrylate, 3-methylbutyl acrylate, 2-methylpentyl acrylate, nonyl acrylate, octyl acrylate, 1-propyl acrylate, 2-ethylhexyl methacrylate, octyl methacrylate, n-dodecyl methacrylate, n-octadecyl methacrylate, n-decyl methacrylate, n-pentyl methacrylate, isobutylene, isoprene, 1,2-butadiene, 1,3-butadiene, 5-methyl-1-hexene, 6-methyl-1-heptene, 4,4-dimethyl-1-pentene, iso-butyl vinyl ether, styrene, 2-methyl styrene, 3-methylstyrene, 4-methyl styrene, 2-t-butyl styrene, 3-t-butyl styrene, 4-t-butyl styrene, and mixtures thereof.

E is a copolymerizable moiety or "endcapping" group. Preferably E is an ethyleneically unsaturated moiety. More preferred is when E is selected from the group consisting of vinyl, allyl, acryloyl, methacryloyl, ethacryloyl, 2-vinylbenzyl, 3-vinylbenzyl, 4-vinylbenzyl, 2-vinylbenzoyl, 3-vinylbenzoyl, 4-vinylbenzoyl, 1-butenyl, 1-propenyl, isobutenyl, cyclohexenyl, cyclopentenyl, and mixtures thereof. Even more preferred is when E is selected from the group consisting of vinyl, allyl, acryloyl, methacryloyl, ethacryloyl, 3-vinylbenzyl, 4-vinylbenzyl, 3-vinylbenzoyl, 4-vinylbenzoyl, 1-butenyl, 1-propenyl, isobutenyl, and mixtures thereof. Most preferred is when E is selected from the group consisting of vinyl, allyl, acryloyl, methacryloyl, ethacryloyl, 3-vinylbenzyl, 4-vinylbenzyl, and mixtures thereof.

Nonlimiting examples of polysiloxane and polyalkylene B macromonomer units useful herein include those selected from the group consisting of acryloyl, methacryloyl, or 3-, or 4-vinylbenzoyl endcapped polymers of polydimethylsiloxane, polydiethylsiloxane, polyphenylmethylsiloxane, polyphenylethylsiloxane, poly(n-butyl acrylate), poly(dodecyl acrylate), poly(2-ethylhexyl acrylate), poly(2-ethylbutyl acrylate), poly(n-ethyl acrylate), poly(n-heptyl acrylate), poly(n-hexyl acrylate), poly(iso-butyl acrylate), poly(iso-decyl acrylate), poly(iso-propyl acrylate), poly(3-methylbutyl acrylate), poly(2-methylpentyl acrylate), poly(nonyl acrylate), poly(octyl acrylate), poly(propyl acrylate), poly (2-ethylhexyl methacrylate), poly(tridecyl methacrylate), poly (hexyl methacrylate), poly(decyl methacrylate), poly(octyl methacrylate), poly(octadecyl methacrylate), poly(dodecyl methacrylate), poly(n-pentyl methacrylate), poly (isobutylene), poly(isoprene), hydrogenated poly(1,2-butadiene), hydrogenated poly(1,4-butadiene), hydrogenated poly(isoprene), poly(1,2-butadiene), poly(1-butene), poly(5-methyl-1-hexene), poly(6-methyl-1-heptene), poly(4,4-dimethyl-1-pentene), poly(iso-butyl vinyl ether), poly[4-t-butyl vinyl benzene-co-2-ethylhexyl acrylate], poly[2-ethylhexyl acrylate-co-octyl acrylamide), poly[2-ethyl vinyl benzene-co-octyl-methacrylate)], and mixtures thereof.

"Copolymer" type B macromonomers containing two or more different randomly repeating monomer units are useful herein. Nonlimiting examples of these "copolymer" type of macromonomers include acryloyl endcapped poly[co(4-t-butyl vinyl benzene)(2,4-dimethyl vinyl benzene)], poly[co(4-t-butyl vinyl benzene)(2-ethylhexyl acrylate)], poly[co(2,4-dimethyl vinyl benzene)(2-ethylhexyl acrylate)], poly[co(2-ethyl vinyl benzene)(octylmethacrylate)], and the like.

Preferred Polymers Of The Present Invention

Nonlimiting examples of preferred polymers of the present invention include those selected from the group consisting of poly[(t-butylacrylate)-graft-poly (dimethylsiloxane)], poly[(4-t- butylstyrene)-graft-poly (dimethylsiloxane)]poly[poly-t-butylacrylate)-graft-poly (isobutylene)], poly[poly(4-t-butylstyrene)-graft-poly (isobutylene)], poly[(t-butylstyrene)-graft-poly(2-ethylhexyl methacrylate)], poly[(4-t-butylacrylate-co-styrene)-graft-poly(isobutylene)], and mixtures thereof.

More specific examples of copolymers of the present invention include the following, where the composition is given as weight percentage of each monomer used in the polymerization reaction (i.e. the weight percentage of the monomers and macromonomers charged).

poly[(t-butylacrylate)-graft-poly(dimethylsiloxane)] having a weight average molecular weight of about 900,000, comprising about 75% t-butylacrylate and about 25% dimethylsiloxane macromonomer with a weight average molecular weight of about 11,000.

poly[(t-butylacrylate)-graft-poly(dimethylsiloxane)]having a weight average molecular weight of about 900,000, comprising about 80% t-butyl acrylate and about 20% dimethylsiloxane macromonomer with a weight average molecular weight of about 15,000.

poly[(t-butylstyrene)-graft-poly(dimethylsiloxane)] having a weight average molecular weight of about 300,000, comprising about 70% t-butyl styrene and about 30% dimethylsiloxane macromonomer with a weight average molecular weight of about 20,000.

poly[(t-butyl acrylate-co-acrylic acid)-graft-polydimethylsiloxane)] having a weight average molecular weight of about 700,000, comprising about 67% t-butyl acrylate, about 3% acrylic acid, and about 30% dimethylsiloxane macromonomer with a weight average molecular weight of about 11,000.

poly[(t-butylacrylate)-graft-poly(dimethylsiloxane)] having a weight average molecular weight of about 1,000,000, comprising about 65% t-butyl acrylate and about 35% dimethylsiloxane macromonomer with a weight average molecular weight of about 30,000.

poly[t-butyl acrylate-co-2-ethylhexylmethacrylate)-graft-poly(dimethylsiloxane)] having a weight average molecular weight of about 700,000, comprising about 70% t-butyl acrylate, about 5% 2-ethylhexyl methacrylate, and about 25% of dimethylsiloxane macromonomer with a weight average molecular weight of about 15,000.

poly[(t-butylstyrene)-graft-poly(2-ethylhexylmethacrylate)] having a weight average molecular weight of about 150,000, comprising about 80% t-butyl styrene and about 20% poly(2-ethylhexylmethacrylate) macromonomer with a weight average molecular weight of about 5000.

poly[(t-butylacrylate-co-styrene)-graft-poly(isobutylene)] having a weight average molecular weight of about 150,000, comprising about 60% t-butyl acrylate, about 20% styrene, and about 20% polyisobutylene macromonomer with a weight average molecular weight of about 10,000.

Volatile Hydrophobic Solvent

The copolymer component of the present invention comprises from about 30% to about 98.5%, preferably from about 60% to about 95%, and more preferably from about 75% to about 95%, based on the weight of the copolymer component, of a volatile, hydrophobic solvent for the hydrophobic copolymer.

The term "volatile", as used herein, means that the solvent exhibits a significant vapor pressure at ambient conditions (e.g., 1 atmosphere at 25° C.), as understood by those skilled in the scientific arts. Specially, the solvent has a boiling point at one atmosphere of about 225° C. or less, preferably about 220° C. or less, more preferably about 215° C. or less, and most preferably about 210° C. or less. In addition, the boiling point of the solvent will generally be at least about 50° C., preferably at least about 90° C. The solvent should also be acceptable for topical application to the hair and the skin.

Suitable volatile hydrophobic solvents are selected from the group consisting of branched chain hydrocarbons, silicones, and mixtures thereof.

Preferred volatile hydrophobic branched chain hydrocarbons useful as the solvent herein contain from about 7 to about 14, more preferably from about 10 to about 13, and most preferably from about 11 to about 12 carbon atom. Saturated hydrocarbons are preferred, although it is not intended to exclude unsaturated hydrocarbons. Examples of such preferred branched chain hydrocarbons include isoparaffins of the above chain sizes. Isoparaffins are commercially available from Exxon Chemical Co; examples include Isopar E ($C_8$–$C_9$ isoparaffins), Isopar™ H and K ($C_{11}$–$C_{12}$ isoparaffins), and Isopar™ L ($C_{11}$–$C_{13}$ isoparaffins). Other suitable branched chain hydrocarbons are isododecane and isoundecane. Isododecane is preferred and is commercially available from Presperse, Inc. (South Plainfield, N.J., USA) as Permethyl™ 99A.

Preferred silicones useful as the volatile hydrophobic solvent herein include volatile siloxanes such as phenyl pentamethyl disiloxane, phenylethylpentamethyl disiloxane, hexamethyl disiloxane, methoxy propylheptamethyl cyclotetrasiloxane, chloropropyl pentamethyl disiloxane, hydroxypropyl pentamethyl disiloxane, octamethyl cyclotetrasiloxane, decamethyl cyclopentasiloxane, and mixtures thereof. More preferred among the silicones are cyclomethicones, examples of which include octamethyl cyclo tetrasiloxane and decamethyl cyclopentasiloxane, which are commonly referred to D4 and D5 cyclomethicone, respectively.

Carrier

The rinse-off hair care compositions of the present invention also comprise a carrier, or a mixture of such carriers, which are suitable for application to hair. The carriers are present at from about 30% to about 99.75%, preferably from about 70% to about 96%, most preferably from about 82% to about 92%, of the composition. As used herein, the phrase "suitable for application to hair" means that the carrier does not damage or negatively affect the aesthetics of hair or cause irritation to skin.

Hair Conditioners

Where the hair care compositions are conditioner compositions, the carrier may comprise gel vehicle materials. This gel vehicle comprises two essential components: a lipid vehicle material and a cationic surfactant vehicle material. Cationic surfactant materials are described in detail below. Gel-type vehicles are generally described in the following documents: Barry, "The Self Bodying Action of the Mixed Emulsifier Sodium Dodecyl Sulfate/Cetyl Alcohol", 28 *J. of Colloid and Interface Science* 82–91 (1968); Barry, et al., "The Self-Bodying Action of Alkyltrimethylammonium Bromides/Cetostearyl Alcohol Mixed Emulsifiers; Influence of Quaternary Chain Length", 35 *J. of Colloid and Interface Science* 689–708 (1971); and Barry, et al., "Rheology of Systems Containing Cetomacrogol 1000—Cetostearyl Alcohol, I. Self Bodying Action", 38 *J. of Colloid and Interface Science* 616–625 (1972).

The gel vehicles may incorporate one or more lipid vehicle materials which are essentially water-insoluble, and contain hydrophobic and hydrophilic moieties. Lipid vehicle materials include naturally or synthetically-derived acids, acid derivatives, alcohols, esters, ethers, ketones, and amides with carbon chains of from about 12 to about 22, preferably from about 16 to about 18, carbon atoms in length. Fatty alcohols and fatty esters are preferred; fatty alcohols are particularly preferred.

Lipid vehicle materials among those useful herein are disclosed in *Bailey's Industrial Oil and Fat Products*, (3rd edition, D. Swern, ed., 1979). Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe, et al., issued Aug. 21, 1979; U.S. Pat. No. 4,269,824, and Villamarin, et al., issued May 26, 1981. Fatty alcohols are also disclosed in British Specification 1,532,585, published Nov. 15, 1978; and Fukushima, et al., "The Effect of Cetostearyl Alcohol in Cosmetic Emulsions", 98 *Cosmetics & Toiletries* 89–112 (1983). Fatty esters included among those useful herein are disclosed in U.S. Pat. No. 3,341,465, Kaufman, et al., issued Sep. 12, 1976 (incorporated by reference herein). If included in the compositions of the present invention, the lipid vehicle material is present at from about 0.1% to about 10.0%, preferably 0.1% to about 5%, of the composition; the cationic surfactant vehicle material is present at from about 0.05% to about 5.0%, preferably 0.1% to about 3%, of the composition.

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl alcohol.

Preferred vehicles for use in the compositions of the present invention include combinations of hydrophobically-modified hydroxyethyl cellulose materials with thickeners (such as xanthan gum), particular surfactants, quaternary ammonium compounds (such as ditallowdimethyl ammonium chloride). These vehicles are described in detail in U.S. Pat. No. 5,100,658, issued to Bolich, R. E., et al. on Mar. 31, 1992; U.S. Pat. No. 5,104,646, issued to Bolich, R. E., et al. on Apr. 14, 1992; U.S. Pat. No. 5,106,609, issued to Bolich, R. E., et al. on Apr. 21, 1992, all incorporated herein by reference.

Shampoos

Where the hair care compositions are shampoo compositions, the carrier may include a surfactant material. The surfactant materials for the shampoo carriers of the invention comprise from about 5% to about 50%, preferably from about 10% to about 30%, most preferably from about 12% to about 25%, of the composition.

Synthetic anionic detergents useful herein, particularly for shampoo compositions, include alkyl and alkyl ether sulfates. These materials have the respective formulae $ROSO_3M$ and $RO(C_2H_4O)_xSO_3M$, wherein R is alkyl or alkenyl of from about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having from about 10 to about 20 carbon atoms. Preferably, R has from about 12 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with about 1 to about 10, and especially about 3, molar proportions of ethylene oxide and the resulting mixture of molecular species, having, for example, an average of 3 moles of ethylene oxide per mole of alcohol, is sulfated and neutralized.

Specific examples of alkyl ether sulfates which may be used in the present invention are sodium coconut alkyl triethylene glycol ether sulfate; sodium tallow alkyl triethylene glycol ether sulfate; and sodium tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide. Such a mixture also comprises from about 0 to about 20% by weight $C_{12-13}$ compounds; from about 60 to about 100% by weight of $C_{14-15-16}$ compounds, from about 0 to about 20% by weight of $C_{17-18-19}$ compounds; from about 3 to about 30% by weight of compounds having a degree of ethoxylation of 0; from about 45 to about 90% by weight of compounds having a degree of ethoxylation of from about 1 to about 4; from about 10 to about 25% by weight of compounds having a degree of ethoxylation of from about 4 to about 8; and from about 0.1 to about 15% by weight of compounds having a degree of ethoxylation greater than about 8.

Another suitable class of anionic surfactants are the water-soluble salts of the organic, sulfuric acid reaction products of the general formula:

$$R^1\text{—}SO_3\text{—}M$$

wherein $R^1$ is chosen from the group consisting of a straight or branched chain, saturated aliphatic hydrocarbon radical having from about 8 to about 24, preferably about 12 to about 18, carbon atoms; and M is a cation. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12-18}$ n-paraffins.

Additional examples of anionic synthetic surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other anionic synthetic surfactants of this variety are set forth in U.S. Pat. Nos. 2,486,921; 2,486,922; and 2,396,278.

Still other anionic synthetic surfactants include the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Other suitable anionic surfactants utilizable herein are olefin sulfonates having about 12 to about 24 carbon atom. The term "olefin sulfonates" is used herein to mean compounds which can be produced by the sulfonation of a-olefins by means of uncomplexed sulfur trioxide, followed by neutralization of the acid reaction mixture in conditions such that any sultones which have been formed in the reaction are hydrolyzed to give the corresponding hydroxyalkanesulfonates. The sulfur trioxide can be liquid or gaseous, and is usually, but not necessarily, diluted by inert diluents, for example by liquid SO2, chlorinated hydrocarbons, etc., when used in the liquid form, or by air, nitrogen, gaseous $SO_2$, etc., when used in the gaseous form.

The a-olefins from which the olefin sulfonates are derived are mono-olefins having about 12 to about 24 carbon atoms, preferably about 14 to about 16 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific a-olefin sulfonate mixture of the above type is described more fully in the U.S. Pat. No. 3,332,880, Pflaumer and Kessler, issued Jul. 25, 1967, incorporated herein by reference.

Another class of anionic organic surfactants are the b-alkyloxy alkane sulfonates. These compounds have the following formula:

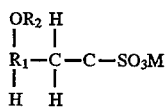

where $R_1$ is a straight chain alkyl group having from about 6 to about 20 carbon atoms, $R_{,2}$ is a lower alkyl group having from about 1 (preferred) to about 3 carbon atoms, and M is a water-soluble cation as herein described.

Specific examples of b-alkyloxy-alkane-1-sulfonates, or alternatively 2-alkyloxy-alkane-1-sulfonates, having low hardness (calcium ion) sensitivity useful herein include: potassium-b-methoxydecanesulfonate, sodium 2-methoxy-tridecanesulfonate, potassium 2-ethoxytetradecylsulfonate, sodium 2-isopropoxyhexadecylsulfonate, lithium 2-t-butoxytetradecylsulfonate, sodium b-methoxyoctadecylsulfonate, and ammonium b-n-propoxydedecylsulfonate.

Many additional nonsoap synthetic anionic surfactants are described in *McCutcheon's, Detergents and Emulsifiers*, 1984 *Annual*, published by Allured Publishing Corporation. Also U.S. Pat. No. 3,929,678, Laughlin et al., issued Dec. 30, 1975, discloses many other anionic as well as other surfactant types and is incorporated herein by reference.

Rinse-off Compositions in General

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to about 12 carbon atoms in either a straight chain or branched chain configuration, with ethylene oxide, the said ethylene oxide being present in mounts equal to from about 10 to about 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

5. Long chain tertiary phosphine oxides corresponding to the following general formula:

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide. 3,6,9-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleydimethylphosphine oxide, 2-hydroxydodecyldimethylphosphine oxide.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Cationic surfactants useful in compositions of the present invention, particularly the conditioner compositions, contain amino or quaternary ammonium hydrophilic moieties which are positively charged when dissolved in the aqueous composition of the present invention. Cationic surfactants among those useful herein are disclosed in the following documents. M. C. Publishing Co., *McCutcheon's, Detergents & Emulsifiers*, (North American edition 1979); Schwartz, et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued June 7, 1983 (the U.S. patents being incorporated by reference herein. If included in the compositions of the present invention, the cationic surfactant is present at from about 0.05% to about 5%.

Among the quaternary ammonium-containing cationic surfactant materials useful herein are those of the general formula:

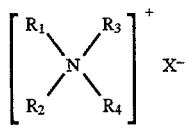

wherein $R_1$–$R_4$ are independently an aliphatic group of from about 1 to about 22 carbon atoms, or an aromatic, alkoxy, polyoxyalkylene, alkylamido, hydroxyalkyl, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups.

Other quaternary ammonium salts useful herein have the formula:

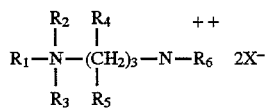

wherein $R_1$ is an aliphatic group having from about 16 to about 22 carbon atoms, $R_2$, $R_3$, $R_4$, $R_5$, and $R_6$ are selected from hydrogen and alkyl having from about 1 to about 4 carbon atoms, and X is an ion selected from halogen, acetate, phosphate, nitrate and alkyl sulfate radicals. Such quaternary ammonium salts include tallow propane diammonium dichloride.

Preferred quaternary ammonium salts include dialkyldimethyl-ammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominantly from 16 to 18 carbon atoms). Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(hydrogenated tallow) dimethyl ammonium chloride is a particularly preferred quaternary ammonium salt.

Salts of primary, secondary and tertiary fatty amines are also preferred cationic surfactant materials. The alkyl groups of such amines preferably have from about 12 to about 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E. O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

Zwitterionic surfactants, useful in shampoos as well as conditioners, are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contain an anionic water-solubilizing group, e.g., carboxy, sulfonate, sulfate, phosphate, or phosphonate. A general formula for these compounds is:

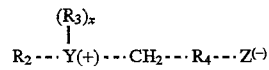

wherein $R_2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R_3$ is an alkyl or monohydroxyalkyl group containing about 1 to about 3 carbon atoms; X is 1 when Y is a sulfur atom, and 2 when Y is a nitrogen or phosphorus atom; $R_4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxy-propane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Other zwitterionics such as betaines are also useful in the present invention. Examples of betaines useful herein include the high alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH(CH$_2$)$_3$ radical is attached to the nitrogen atom of the betaine are also useful in this invention.

Examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

The above-mentioned surfactants can be used alone or in combination in the hair care compositions of the present invention. The alkyl sates, ethoxylated alkyl sulfates, and mixtures thereof are preferred for use herein.

The hair care compositions herein can contain a variety of other optional components suitable for rendering such compositions more cosmetically or aesthetically acceptable or to provide them with additional usage benefits. Such conventional optional ingredients are well-known to those skilled in the art, e.g., pearlescent aids, such as ethylene glycol distearate; preservatives, such as benzyl alcohol, methyl paraben, propyl paraben and imidazolidinyl urea; thickeners and viscosity modifiers, such as a diethanolamide of a long chain fatty acid (e.g., PEG 3 lauric diethanolamide), cocomonoethanol amide, dimethicone copolyols, guar gum, methyl cellulose, starches and starch derivatives; fatty alcohols, such as cetearyl alcohol; sodium chloride; sodium sulfate; polyvinyl alcohol; ethyl alcohol; pH adjusting agents, such as citric acid, sodium citrate, succinic acid, phosphoric acid, sodium hydroxide, and sodium carbonate; coloring agents, such as any of the FD&C or D&C dyes; hair oxidizing (bleaching) agents, such as hydrogen peroxide, perborate and persulfate salts; hair reducing agents, such as the thioglycolates; perfumes; sequestering agents, such as disodium ethylenediamine tetra-acetate; and copolymer plasticizing agents, such as glycerin and propylene glycol. Such optional ingredients generally are used individually at levels of from about 0.01% to about 10.0%, preferably from about 0.05% to about 5.0%, of the composition.

Plasticizers

Plasticization of the copolymers of the present invention can dramatically hinder the removability of the copolymers with normal shampooing. Without being limited by theory, it is believed that plasticization of the copolymer softens the polymer film on the hair, thereby decreasing the cohesive breaking stress and increasing the cohesive breaking strain of the polymer. This in turn results in the fracturing of the polymer film during shampooing rather than breaking of the adhesive bond to the hair. This results in incomplete removal of the copolymer and an eventual build-up of residue on the hair.

The compositions of the present invention are limited in the amount of materials which act as copolymer plasticizers. In preferred embodiments, the compositions of the present invention should be substantially free of such plasticizing materials, i.e. they should contain less than about 2%, preferably less than about 1%, and more preferably less than about 0.5%, by weight, of such plasticizer materials. Plasticizing materials are generally relatively non-volatile organic liquids compatible with the copolymer component. By "non-volatile" it is meant that the boiling point of the liquids is greater than or equal to 260 about ° C. A nonlimiting list of exemplary materials which may act as plasticizers of the copolymers of the present invention includes diisobutyl adipate, acetyl tri-n-butyl citrate, di(2-ethyl hexyl) azelate, 2-ethyl hexyl diphenyl phosphate, diisoctyl isophthalate, isooctyl benzyl phthalate, butyl stearate, tri-2-ethyl hexyl trimellitate, N-octyl neopentanoate, diisostearyl malate, colloidal fumed silica (such as Cab-O-Sil®, sold by Cabot Corp.) and most perfumed materials.

pH

The pH of the present compositions should be between about 3 and about 9, preferably between about 4 and about 8.

Method of Use

The hair care compositions of the present invention are used in conventional ways to provide the styling and hold benefits of the present invention. Such method of use depends upon the type of composition employed but generally involves application of an effective amount of the product to the hair, which is preferably wet or damp. The products are subsequently rinsed from the hair before drying and styling.

The methods of the present invention involve application of an effective amount of the compositions of the present invention to the hair. By "effective amount" is meant an amount sufficient to provide the hair styling and holding benefits desired considering the length and texture of the hair, the type of product used, and the style and hold desired. Typical amounts are generally from about 0.5 g to about 50 g of product.

Residue Index

The rinse-off hair care compositions of the present invention have a residue index on hair of about 20 or greater, preferably of about 35 or greater, and more preferably of about 50 or greater.

The residue index, on hair, of the compositions of the present invention, can be measured by various in vitro techniques. For example, a preferred method is one wherein the compositions are evaluated on human hair switches in repeated cycles comprising the steps of shampooing the hair switch with a surfactant solution, treating the hair switch with the rinse-off composition to be evaluated, rinsing the hair switch, and drying the hair switch. The hair switch is evaluated for the presence of residue after a defined number of cycles.

For example, for determining a residue index, it is found particularly useful to visually examine the hair switch for the presence of a visible residue after the completion of multiples of five treatment cycles, e.g. after 5, 10, 15, 20, 25, and 30 cycles, and so forth, until the desired visual end point is achieved. The residue index is defined herein as the number of treatment cycles, in 5 unit increments, after which a visible residue is first visually observed on the hair.

As mentioned above, the compositions of the present invention do not leave a visible residue on the hair switches, i.e. they do not exhibit a visible residue until after about 20 or more cycles. In other words, such compositions have a residue index of about 20 or greater. More preferred are compositions which do not exhibit a visible residue until after about 35 or more cycles, in other words such compositions have a residue index of about 35 or greater. Even more preferred are compositions which do not exhibit a visible residue until after about 50 or more cycles, in other words such compositions have a residue index of about 50 or greater. Even though there is no upper limit on the residue index, it is recognized that the higher the index, the better the performance of the composition in not leaving a visible residue upon the hair.

In the present invention the preferred method for measuring the residue index is as follows:

The residue index measurements are made on switches of human hair that have been arranged in the shape of a ponytail, i.e the hair is firmly glued together at one end. Switches containing twenty grams of dark brown, fine, virgin hair having an overall length of about 8 inches are used herein. These switches contain hair fibers having an overall length of about 8 inches and an average hair fiber diameter of about 40 to about 70 microns. The average hair fiber diameter is determined by making measurements on at least 10 hair fibers in the switch sample. The hair fiber diameter can be verified using a micrometer or standard microscopic techniques familiar to one of ordinary skill in the art of cosmetic science. By "virgin hair" is meant that the hair has not been subjected to chemical treatments such as bleaching or perming. The hair switches can be examined by standard electron microscopic techniques to evaluate the quality of the hair, e.g. the condition of the hair cuticles can be examined.

It is found convenient to evaluate the residue index of a rinse-off composition on several hair switches. The hair switches are wetted under a water spray tap with a water temperature of 100° F. and at a flow rate of about 1 gallon per minute. It is preferable to use gloved hands (e.g. latex surgical gloves) when handling the hair to avoid contaminating the hair samples with skin oils and other materials. Using a syringe, 1 cc of a surfactant solution having the following percent weight percent composition is applied to the hair switch and worked into the hair for approximately 15 seconds.

| Surfactant Solution For Residue Index Method | |
|---|---|
| Ingredient | Weight Percent |
| Distilled Water | 78% |
| Ammonium Laureth-3 Sulfate[1] | 13% |
| Ammonium Lauryl Sulfate | 9% |

[1]Having an average of about 3 molecules of ethylene oxide incorporated per molecule (or alternatively, 3 moles of ethylene oxide per mole of surfactant).

The hair switch is next rinsed with water (100° F.; 1 gallon/minute) for 15 seconds wherein the hair switch is gently squeezed three times while running the fingers along the length of the hair switch. The excess water is squeezed from the hair. Using a syringe, the switch is then treated with 6 cc of the rinse-off composition to be evaluated which is worked into the hair for approximately 15 seconds. The hair switch is next rinsed with water (100° F., 1 gallon/minute) for approximately 15 seconds wherein the hair switch is gentle squeezed twelve times while running the fingers along the length of the hair switch. The excess water is squeezed from the hair. The hair switch is next hung to dry in a chamber having an air temperature of about 100° F., in which the air flow is minimized to avoid disturbing the switches, for about 60 minutes. These steps of surfactant washing, rinsing, treatment with the rinse-off composition, rinsing, and air-drying constitute one cycle. After five such cycles are completed, the hair switch is visually examined while ungloved fingers are run through the switch to determine whether there is any visible composition residue on the hair strands. The residue must be one that is encircling the hair fibers. The presence of such encircling residues can be verified using any magnification techniques available to one of ordinary skill in the art. If no visible encircling residue is observed, additional groups of five cycles of surfactant washing, rinsing, treatment with the rinse-off composition, rinsing, and air-drying are repeated until a visible encircling residue is observed.

Once it is established that an encircling residue is present. The hair switch is subjected to two vigorous washes with 1 cc of the surfactant solution described above, each followed by a 15 second rinsing (100° F. water; 1 gallon/minute). If the residue remains after these two additional surfactant washings, the rinse-off composition is defined as having a residue index corresponding to that number of cycles completed prior to the two additional surfactant washings. If no visible residue is observed, after the two additional surfactant washings, groups of five additional treatment cycles are performed on other hair switch substrates until a visible residue is observed.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLE 1 and 2

The following synthetic procedure is exemplary of the methods useful for synthesizing the copolymers of the present invention.

EXAMPLE 1

Synthesis of Poly(4-t-butyl styrene)-graft-[poly (isobutylene]

A. Synthesis of Acryloyl Endcapped Polyisobutylene Macromonomer

Prepare a solution of 100 grams (0.024 mol) hydroxyl endcapped polyisobutylene polymer (PIB-OH) having a weight average molecular weight of 4,172 g/mol by conventional living carbocationic polymerization of isobutylene (for example, as described in G. Kaszas, Poly. Bull., 20, 413 (1989). Add a two fold mole excess (4.84 g, 0.048 mol) triethylamine to the solution. Add this solution dropwise to a solution of acryloyl chloride (4.35 g, 0.048 mol) in dry methylene chloride (100 g) at 0° C. Stir for about 12 hours at room temperature, filter the mixture and evaporate the excess triethylamine and methylene chloride to obtain acryloyl endcapped polyisobutylene macromonomer.

B. Batch Synthesis Of The Copolymer

Place 5 parts acrylic acid, 75 parts t-butyl acrylate, and 20 parts polyisobutylene macromonomer (10,000 MW) from Experimental 1A in a flask. Add sufficient tetrahydrofuran as the reaction solvent to produce a final monomer concentration of 20%. Purge the vessel with an inert atmosphere, preferably nitrogen or argon. Add initiator, (2,2'-azobisisobutyronitrile) to a level appropriate for the desired molecular weight. Typically this is in the range of 0.5% to 1.0% by weight relative to the amount of monomer. Heat to 60° C. and maintain this temperature for 48 hours while agitating. Terminate the reaction by cooling to room temperature. The polymer is purified by drying off the reaction solvent in an oven.

C. Semi-Continuous Synthesis Of The Copolymer

Place 5 parts acrylic acid, 75 parts t-butyl acrylate, and 20 parts polyisobutylene macromonomer (10,000 MW) from Experimental 1A in a flask. Add 300 parts tetrahydrofuran as the reaction solvent to produce a final monomer concentration of 20%. Purge the vessel with an inert atmosphere, e.g. nitrogen or argon. Add initiator, (2,2'-azobisisobutyronitrile) as in Experimental 1B. Heat to 60° C. and maintain this temperature. After polymerization of these monomers has proceeded about 15 minutes to about 1 hour, e.g. about 30 minutes, add a second monomer charge of 20 parts acrylic acid and 60 parts t-butyl acrylate, to give a final total monomer charge of approximately 40% by weight. Maintain at temperature for 48 hours. Terminate the reaction by cooling to room temperature. The polymer is purified by drying off the reaction solvent in an oven.

EXAMPLE 2

Synthesis of Poly[(t-butyl acrylate)-graft-polydimethylsiloxane)]

Place 75 parts of t-butyl acrylate and 25 parts of polydimethylsiloxane macromonomer (11,000 MW) (commercially available from 3M, St. Paul, Minn.) in a flask. Add sufficient ethyl acetate as the reaction solvent to produce a final monomer concentration of 20%. Purge the vessel with an inert atmosphere, preferably nitrogen or argon. Add initiator, (2,2'-azobisisobutyronitrile) to a level appropriate for the desired molecular weight. Typically this is in the range of about 0.25% to about 1.0% by weight relative to the amount of monomer. Heat to 60° C. and maintain this temperature for 48 hours while agitating. Terminate the reaction by cooling to room temperature. The polymer is purified by drying off the reaction solvent in an oven.

By varying the monomers and macromonomers used, the general procedures given above in Examples 1 and 2 are used to prepare other macromonomers and copolymers of the present invention.

EXAMPLES 3–11

The hair care composition illustrated in Examples 3–11 are useful for application to the hair to provide a styling and hold benefit.

These composition have a residue index of about 20 or greater.

The following Table 1 defines nonlimiting examples of copolymers that can be used in the hair care compositions shown in Examples 3–11. Each of the Examples 3–10 is illustrated with Copolymer #1, however, any of the other copolymers from Table 1, or any other copolymers of the present invention can be employed. In Table 1, the relative weight percentages of the monomers and macromonomers are given.

Table 1

Copolymer #1 poly[(t-butylacrylate)-graft-poly(dimethylsiloxane)] having a weight average molecular weight of about 900,000, comprising about 75% t-butylacrylate and about 25% dimethylsiloxane macromonomer with a weight average molecular weight of about 11,000.

Copolymer#2 poly[(t-butylacrylate)-graft-poly(dimethylsiloxane)] having a weight average molecular weight of about 900,000, comprising about 80% t-butyl acrylate and about 20% dimethylsiloxane macromonomer with a weight average molecular weight of about 15,000.

Copolymer #3 poly[(t-butylstyrene)-graft-poly(dimethylsiloxane)] having a weight average molecular weight of about 300,000, comprising about 70% t-butyl styrene and about 30% dimethylsiloxane macromonomer with a weight average molecular weight of about 20,000.

Copolymer #4 poly[(t-butyl acrylate-co-acrylic acid)-graft-polydimethylsiloxane)] having a weight average molecular weight of about 700,000, comprising about 67% t-butyl acrylate, about 3% acrylic acid, and about 30% dimethylsiloxane macromonomer with a weight average molecular weight of about 11,000.

Copolymer #5 poly[(t-butylacrylate)-graft-poly(dimethylsiloxane)] having a weight average molecular weight of about 1,000,000, comprising about 65% t-butyl acrylate and about 35% dimethylsiloxane macromonomer with a weight average molecular weight of about 30,000.

Copolymer #6 poly[t-butyl acrylate-co-2-ethylhexylmethacrylate)-graft-poly(dimethylsiloxane)] having a weight average molecular weight of about 700,000, comprising about 70% t-butyl acrylate, about 5% 2-ethylhexyl methacrylate, and about 25% of dimethylsiloxane macromonomer with a weight average molecular weight of about 15,000.

Copolymer#7 poly[(t-butylstyrene)-graft-poly(2-ethylhexylmethacrylate)] having a weight average molecular weight of about 150,000, comprising about 80% t-butyl styrene and about 20% poly(2-ethylhexylmethacrylate) macromonomer with a weight average molecular weight of about 5000.

Copolymer#8 poly[(t-butylacrylate-co-styrene)-graft-poly(isobutylene)] having a weight average molecular weight of about 150,000, comprising about 60% t-butyl acrylate, about 20% styrene, and about 20% polyisobutylene macromonomer with a weight average molecular weight of about 10,000.

EXAMPLE 3

The following is a rinse-off hair conditioner composition representative of the present invention.

| Ingredient | Weight % |
| --- | --- |
| Water | Q.S. 100 |
| Hydrophobically Modified Hydroxyethylcellulose[1] | 0.25 |
| Stearalkonium Chloride | 0.87 |
| Cetyl Alcohol | 1.85 |
| Stearyl Alcohol | 0.21 |
| Stearamidopropyl Dimethylamine | 0.50 |
| Dimethicone Gum (CF1213)[2] | 2.33 |
| Methylchloroisothiaolinone (and) Methylisothiazolinone | 0.03 |
| Perfume | 0.33 |
| Copolymer # 1 | 2.00 |
| Trimethylsiloxysilicate[2] | 0.21 |
| Cyclomethicone D4 | 11.30 |

[1] Available as Polysurf 67 from Aqualon Chemical Company.
[2] Commercially available from General Electric.

This compositions is prepared by dissolving the copolymer #1 in Cyclomethicone D4 (solvent). The dimethicone gum is added to this solution. The other components (except for the methylchloroisothiazolinone (and methylisothiazolineone and the perfume) are mixed in a separate vessel at a temperature high enough (80 C) to melt the solids. The polymer/solvent mixture and the dimethicone gum are added separately to the other components after those have been cooled to at least 45 C. Finally, the methylchloroisothiazolinone (and) methylisothiazolinone and perfume are added, and the product cooled to ambient.

EXAMPLE 4

The following is a hair conditioner composition representative of the present invention.

| Ingredient | Weight % |
| --- | --- |
| Water | Q.S. to 100% |
| Hydroxyethyl Cellulose | 0.50% |
| Hydrogenated Ditallowdimethyl Amonium Chloride | 0.85% |
| Cetyl Alcohol | 0.90% |
| Stearyl Alcohol | 0.81% |
| Ceteareth-20 | 0.50% |
| Stearamidopropyl Dimethylamine | 0.22% |
| Dimethicone Gum (CF1213)[1] | 1.33% |
| Methylchloroisothiaolinone (and) Methylisothiazolinone | 0.03 |
| Perfume | 0.33% |
| Copolymer # 1 | 2.50% |
| Cyclomethicone D4/D5 Blend [90/10] | 11.30% |

[1] Commercially available from General Electric.

This product is prepared by dissolving the copolymer #1 in the cyclomethicone D4/D5 blend (solvent). The other components (except the methylchloroisothiazolinone (and) methylisothiazolinone and perfume) are mixed in a separate vessel at a temperature high enough (80 C)) to melt the solids. The polymer/solvent mixture and the dimethicone gum are added separately to the other components after those have been cooled to at least 45 C. Finally, the methylchloroisothiazolinone (and) methylisothiazolinone and perfume are added, and the product is cooled to ambient.

EXAMPLE 5

The following is a hair shampoo composition representative of the present invention.

| Ingredient | Weight % |
| --- | --- |
| Water | Q.S. to 100% |
| Ammonium Lauryl Sulfate | 3.14% |
| Ammonium Laureth Sulfate | 13.56% |
| Cetyl Alcohol | 0.45% |
| Stearyl Alcohol | 0.19% |
| Coco Monoethanol Amide | 3.00% |
| Ethylene Glycol Distearate | 2.00% |
| Tricetyl Methyl Ammonium Chloride | 0.50% |
| Methylchloroisothiaolinone (and) Methylisothiazolinone | 0.03 |
| Perfume | 0.20% |
| Copolymer # 1 | 4.00% |
| Isododecane | 7.40% |

This product is prepared by dissolving the copolymer #1 in isododecane (solvent). The other components are mixed in a separate vessel at a temperature high enough to melt the solids. The polymer/solvent mixture is added to the other components with mixing after those have been cooled.

EXAMPLE 6

The following is a hair shampoo composition representative of the present invention.

| Ingredient | Weight % |
| --- | --- |
| Water | Q.S. to 100% |
| Cocoamidopropyl Betaine | 8.30% |
| Ammonium Lauryl Sulfate | 2.12% |
| Ammonium Laureth Sulfate | 6.35% |
| Coco Monoethanol Amide | 1.50% |
| Hydroxypropyl Methyl Cellulose | 0.25% |
| Ethylene Glycol Distearate | 1.50% |
| Tricetyl Methyl Ammonium Chloride | 0.50% |
| Methylchloroisothiaolinone (and) Methylisothiazolinone | 0.03 |
| Perfume | 0.20% |
| Copolymer # 1 | 3.00% |
| Isododecane | 10.00% |

This product is prepared by dissolving the copolymer #1 in the isododecane). The other components are mixed in a separate vessel at a temperature high enough to melt the solids. The polymer/solvent solution is added to the other components after those have been cooled.

EXAMPLE 7

The following is a rinse-off hair styling gel composition representative of the present invention.

| Ingredient | Weight % |
| --- | --- |
| Polymer-Solvent Mix | |
| Copolymer # 1 | 1.25% |
| C11–C12 Isoparaffins[1] | 3.75% |
| Premix | |
| Water | 43.00% |
| Hydrogenated Ditallowdimonium Chloride | 1.00% |

-continued

| Ingredient | Weight % |
| --- | --- |
| Main Mix | |
| Water | 50.00% |
| Carbomer[2] | 0.75% |
| Panthenol | 0.05% |
| Perfume | 0.20% |

[1]Available as Isopahr H from Exxon Chemicals.
[2]Available as Carbopol 940 from B. F. Goodrich.

This composition is prepared by dissolving the copolymer #1 in the C11–C12 isoparaffins. The hydrogenated ditallowdimonium chloride is mixed with water at 80 C. The polymer-solvent mixture is then added at either high or low temperature to the ditallowdimonium chloride mixture. The resulting mixture is added with mixing to the remaining ingredients which are first mixed together in a separate vessel.

EXAMPLE 8

The following is a rinse-off hair spray-on gel composition representative of the present invention.

| Ingredient | Weight % |
| --- | --- |
| Water | Q.S. to 100% |
| Tallowtrimonium Chloride | 0.10% |
| Hydrogenated Ditallowdimonium Chloride | 0.90% |
| Panthenol | 0.05% |
| Perfume | 0.20% |
| Copolymer # 1 | 1.00% |
| Hexamethyl disiloxane | 3.00% |

This composition is prepared by dissolving the copolymer #1 in the hexamethyl disiloxane. The other ingredients are mixed in a separate vessel at a temperature high enough, about 70° C. to melt the solids. The polymer/solvent solution is added to the other components at either high or low temperature.

EXAMPLE 9

The following is a hair styling rinse composition representative of the present invention.

| Ingredient | Weight % |
| --- | --- |
| Premix A | |
| Water | 4.98% |
| Ditallowdimonium Chloride | 1.43% |
| Dimethicone Gum (CF1213)[1] | 2.33% |
| Amodimethicone | 0.10% |
| Premix B | |
| Water | 9.97% |
| Stearalkonium Chloride | 0.30% |
| Panthenol DL | 0.225% |
| Pantyl Ethyl Ether | 0.025% |
| Main Mix | |
| Water | 67.49% |
| Hydrophobically Modified Hydroxyethylcellulose[2] | 1.23% |
| Xanthan Gum | 0.25% |
| Citric Acid | 0.02% |
| Sodium Citrate | 0.09% |
| Cetyl Alcohol | 0.12% |
| Stearyl Alcohol | 0.08% |

-continued

| Ingredient | Weight % |
| --- | --- |
| Polymer-Solvent Mixture | |
| Copolymer # 1 | 1.75% |
| Cyclomethicone D4/D5 Blend [70/30] | 8.54% |
| Trimethylsiloxysilicate (SS4230)[1] | 0.21% |
| Preservatives and Fragrance | |
| Methylchloroisothiaolinone (and) Methylisothiazolinone | 0.03 |
| Benzyl Alcohol | 0.50% |
| Perfume | 0.33% |

[1]Commercially available from GE
[2]Available from Aqualon Chemical Company as Polysurf 67.

The polymer-solvent mixture is prepared by dissolving the copolymer #1 in the cyclomethicone D4/D5 blend (solvent) and the trimethylsiloxysilicate is added. Premixes A and B are prepared separately by combining the indicated ingredients at 70° C. Separately, the Main Mix is also prepared by mixing the indicated ingredients. Premix A is put through a colloid mill and is cooled to 38° C. The polymer-solvent mixture, the methylchloroisothiazolinone (and) the methylisothiazolinone, and the perfume are added to the Main Mix which is milled and cooled to 38° C. Next, the Premixes A and B are then added. Next, benzyl alcohol is added.

EXAMPLE 10

The following is a hair styling rinse composition representative of the present invention.

| Ingredient | Weight % |
| --- | --- |
| Premix A | |
| Water | 4.67% |
| Ditallowdimonium Chloride (Varisoft 470) | 1.00% |
| Dimethicone Gum (15% in Cyclomethicone D5) | 1.00% |
| Amodimethicone | 0.40% |
| Premix B | |
| Water | 9.36% |
| Stearalkonium Chloride | 0.15% |
| D,L-Panthenol | 0.225% |
| Panthyl Ethyl Ether | 0.025% |
| Main Mix | |
| Water | 63.53% |
| Hydrophobically Modified Hydroxyethylcellulose | 1.00% |
| Xanthan Gum | 0.10% |
| Citric Acid | 0.02% |
| Sodium Citrate | 0.09% |
| Cetyl Alcohol | 0.60% |
| Stearyl Alcohol | 0.40% |
| Polymer-Solvent Mixture | |
| Copolymer # 1 | 2.50% |
| Cyclomethicone D4/D5 Blend [95/5] | 14.17% |
| Methylchloroisothiaolinone (and) Methylisothiazolinone | 0.03 |
| Perfume | 0.33% |
| Benzyl Alcohol | 0.50% |

This composition is prepared by dissolving the copolymer #1 in the cyclomethicone D4/D5 blend (solvent). Premixes A and B are prepared separately by combining the indicated ingredients at 70° C. Separately, the Main Mix is also prepared by mixing the indicated ingredients. Premix A is put through a colloid mill and is cooled to 38° C. The polymer-solvent mixture, the methylchloroisothiazolinone (and) the methylisothiazolinone, and the perfume are added to the Main Mix which is milled and cooled to 38° C. Next, the Premixes A and B are then added. Next, benzyl alcohol is added.

EXAMPLE 11

The following is a rinse-off hair styling mousse composition representative of the present invention.

| Ingredient | Weight % |
|---|---|
| Water | Q.S. to 100% |
| Tallowtrimonium Chloride | 0.10% |
| Hydrogenated Ditallowdimonium Chloride | 0.90% |
| Lauramine Oxide | 0.20% |
| Panthenol | 0.05% |
| Perfume | 0.20% |
| Copolymer # 1 | 1.00% |
| Hexamethyl disiloxane | 3.00% |
| Isobutane | 7.00% |

This composition is prepared by dissolving the copolymer #1 in hexamethyl disiloxane (solvent). The other components (except isobutane) are mixed in a separate vessel at a temperature high enough (70° C.) to melt the solids. The polymer/solvent solution is added to the other components after those have been cooled. Aluminum aerosol cans are then filled with 95 parts of this batch, affixed with a valve which is crimped into position, and lastly pressure filled with 5 parts Isobutane.

What is claimed is:

1. A rinse-off hair case composition comprising:
    (A) from about 0.25% to about 70% by weight of said composition of a copolymer component, comprising:
        (i) from about 1.5% to about 70% by weight of said copolymer component, of a hydrophobic copolymer having a weight average molecular weight from about 10,000 to about 5,000,000, said copolymer comprising a polymeric organic backbone and hydrophobic polymeric side chains grafted to said backbone, wherein said copolymer is formed from the copolymerization of randomly repeating monomer units, herein designated A, and polyalkylene macromonomer units, herein designated B, wherein said copolymer comprises:
            (a) from about 50% to about 85% by weight of said copolymer of said A monomer units, wherein said A monomer units are monomer units copolymerizable with said B polyalkylene macromonomer units; and
            (b) from about 15% to about 50% by weight of said copolymer of said B polyalkylene macromonomer units wherein said B polyalkylene macromonomer units are hydrophobic polyalkylene macromonomer units having a polymeric alkylene portion and a moiety copolymerizable with said A monomer units,
        and wherein the weight percent of said copolymer in said rinse-off hair care composition is from about 0.10% to about 7%; and
        (ii) from about 30% to about 98.5% by weight of said copolymer component of a volatile hydrophobic solvent having a boiling point at 1 atmosphere of about 225° C. or less; and
    (B) from about 30% to about 99.75% by weight of said composition of a carrier suitable for application to hair, wherein said rinse-off hair care composition has a residue index on hair of about 20 or greater.

2. A rinse-off hair care composition according to claim 1 wherein said composition has a residue index on hair of about 50 or greater.

3. A composition according to claim 2 wherein said A monomer units comprise hydrophobic monomers selected from the group consisting of unsaturated carboxylic acid esters of C1–C18 alcohols, unsaturated alcohols, unsaturated hydrocarbons, aromatic hydrocarbons containing unsaturated alkyl groups, vinyl esters of carboxylic acids, vinyl ethers, allyl esters of carboxylic acids, allyl ethers, and mixtures thereof.

4. A composition according to claim 3 wherein said A monomer units comprise hydrophobic monomers selected from the group consisting of n-butyl methacrylate, isobutyl methacrylate, t-butyl acrylate, t-butyl methacrylate, 2-ethylhexyl methacrylate, methyl methacrylate, indene, norbornylene, β-pinene, α-pinene, vinyl pivalate, vinyl neononanoate, dicyclopentenyl acrylate, 4-biphenyl acrylate, pentachlorophenyl acrylate, 3,5-dimethyladamantyl acrylate, 3,5-dimethyladamantyl methacrylate, 4-methoxycarbonylphenyl methacrylate, trimethylsilyl methacrylate, t-butyl styrene and mixtures thereof.

5. A composition according to claim 3 wherein said B macromonomer has a weight average molecular weight of about 5,000 to about 50,000.

6. A composition according to claim 5 wherein said polyalkylene macromonomers corresponding to the formula

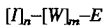

wherein I is an initiator moiety, n is an integer of 0 or 1, W is a hydrophobic monomer unit, E is an endcapping group, and m is an integer from about 10 to about 2000.

7. A composition according to claim 6 wherein I is selected from the group consisting of initiators selected from the group consisting of hydrogen ion, hydrogen radical, hydride ion, hydroxide ion, hydroxyl radical, peroxide radical, peroxide anion, C1–C20 carbocations, C1–C20 carbanions C1–C20 carbon radicals, C1–C20 aliphatic alkoxy anions, C1–C20 aromatic alkoxy anions, ammonium ion, C114 C20 alkyl substituted ammonium ions, C1–C20 alkoxy substituted ammonium ions, and mixtures thereof, W is hydrophobic monomer unit selected from the group consisting of n-butyl acrylate, dodecyl acrylate, ethyl acrylate, 2-ethybutyl acrylate, n-heptyl acrylate, n-hexyl acrylate, iso-butyl acrylate, iso-decyl acrylate, iso-propyl acrylate, 3-methylbutyl acrylate, 2-methylpentyl acrylate, nonyl acrylate, octyl acrylate, 1-propyl acrylate, 2-ethylhexyl methacrylate, octyl methacrylate, n-dodecyl methacrylate, n-octadecyl methacrylate, n-decyl methacrylate, n-pentyl methacrylate, isobutylene, isoprene, 1,2-butadiene, 1,3-butadiene, 5-methyl-1-hexene, 6-methyl-1-heptene, 4,4-dimethyl-1-pentene, iso-butyl vinyl ether, styrene, 2-methyl styrene, 3-methylstyrene, 4-methyl styrene, 2-t-butyl styrene, and mixtures thereof, and E is an endcapping group selected from the group consisting of vinyl, allyl, acryloyl, methacryloyl, ethacryloyl, 3-vinylbenzyl, 4-vinylbenzyl, 3-vinylbenzoyl, 4-vinylbenzoyl, 1-butenyl, 1-propenyl, isobutenyl, and mixtures thereof.

8. A composition according to claim 5, wherein said B macromonomer units are selected from the group consisting of acryloyl, methacryloyl, or 2-vinylbenzyl 3-vinylbenzyl, or 4-vinylbenzyl endcapped polymers of poly(n-butyl acrylate), poly(dodecyl acrylate), poly(2-ethylhexyl acrylate), poly(2-ethylbutyl acrylate), poly(n-ethyl acrylate), poly(n-heptyl acrylate), poly(n-hexyl acrylate), poly(isobutyl acrylate), poly(iso-decyl acrylate, poly(iso-propyl acrylate), poly(3-methylbutyl acrylate), poly(2-methylpentyl acrylate), poly(nonyl acrylate), poly(octyl acrylate), poly(propyl acrylate), poly (2-ethylhexyl methacrylate), poly(tridecyl methacrylate), poly(hexyl methacrylate), poly(decyl methacrylate), poly(octyl methacrylate), poly(octadecyl methacrylate), poly(dodecyl methacrylate), poly(n-pentyl methacrylate), poly(isobutylene), poly(isoprene), hydrogenated poly(1,2-butadiene), hydrogenated poly(1,4-butadiene), hydrogenated poly(isoprene), poly(1,2-butadiene), poly(1-butene), poly(5-methyl-1-hexene), poly(6-methyl-1-heptene), poly(4,4-dimethyl-1-pentene), poly(iso-butyl vinyl ether), poly(4-t-butyl vinyl benzene-co-2-ethylhexyl acrylate), poly(2-ethylhexyl acrylate-co-octyl acrylamide), poly(2-ethyl vinyl benzene-co-octyl methacrylate), and mixtures thereof.

9. A composition according to claim 1, wherein said hydrophobic copolymer is selected from the group consisting of poly(poly-t-butylacrylate)-graft-poly(isobutylene), poly(4-t-butylstyrene)-graft-poly(isobutylene), poly(t-butylstyrene)-graft-poly(2-ethylhexyl methacrylate), poly) 4-t-butylacrylate-co-styrene)-graft-poly(isobutylene), and mixtures thereof.

10. A composition according to claim 9 wherein said hydrophobic volatile solvent is selected from the group consisting of C7–C14 branched hydrocarbons, cyclomethicones, and mixtures thereof.

11. A composition according to claim 1 in the form of a conditioner wherein said carrier comprises from about 0.1% to about 10.0% by weight of the total rinse-off composition of a lipid material and from about 0.05% to about 5% by weight of the total rinse-off composition of a cationic surfactant.

12. A composition according to claim 11 wherein said cationic surfactant is a quaternary ammonium surfactant.

13. A composition according to claim 12 wherein said lipid material is selected from the group consisting of cetyl alcohol, stearyl alcohol, cetyl palmitate, glyceryl monostearate, and mixtures thereof.

14. A composition according to claim 1 in the form of a shampoo wherein said composition further comprises from about 10% to about 30% by weight of the total rinse-off composition of one or more surfactants.

15. A composition according to claim 14 wherein said surfactant is selected from the group consisting of alkyl sulfates, ethoxylated alkyl sulfates, and mixtures thereof.

16. A method of styling hair comprising applying to the hair an effective amount of a composition according to claim 1.

17. A method of holding hair comprising applying to the hair an effective amount of a composition according to claim 1.

* * * * *

UNITED STATES PATENT AND TRADEMARK OFFICE
CERTIFICATE OF CORRECTION

PATENT NO. : 5,653,969
DATED : August 5, 1997
INVENTOR(S) : Jose Antonio Carballada et al.

It is certified that error appears in the above-identified patent and that said Letters Patent is hereby corrected as shown below:

At column 1, line 22 "bends" should read --bonds--.

At column 1, line 28 "bends" should read --bonds--.

At column 1, line 31 "bending" should read --bonding--.

At column 1, line 67 "et at," should read --et al.,--.

At column 2, line 1 "et at." should read --et al.--.

At column 2, line 4 "et at." should read --et al.--.

At column 5, line 55 "therein." should read --therein).--.

At column 6, line 37 "1992 all" should read --1992, all--.

At column 9, line 10 "$C_1$-$C_{14}$" should read --$C_1$-$C_{10}$--.

At column 9, line 42 "40% more" should read --40%, more--.

At column 11, line 3 "(dimethylsiloxane)]poly" should read --(dimethylsiloxane)], poly--.

At column 12, line 12 "atom" should read --atoms--.

At column 14, line 56 "atom" should read --atoms--.

At column 14, line 65 "SO2" should read --$SO_2$--.

At column 15, line 28 "R,2" should read --$R_2$--.

At column 15, line 39 "propoxydedecylsulfonate" should read --propoxydodecylsulfonate--.

At column 15, line 59 "mounts" should read --amounts--.

At column 17, line 13 "documents." should read --documents:--.

At column 17, line 21 "herein." should read --herein).--.

UNITED STATES PATENT AND TRADEMARK OFFICE
CERTIFICATE OF CORRECTION

PATENT NO. : 5,653,969
DATED : August 5, 1997
INVENTOR(S) : Jose Antonio Carballada et al.

It is certified that error appears in the above-identified patent and that said Letters Patent is hereby corrected as shown below:

At column 18, line 41 "contain" should read --contains--.

At column 19, line 51 "sates" should read --sulfates--.

At column 20, line 41 "perfumed" should read --perfume--.

At column 29, line 31 "case" should read --care--.

At column 29, line 52 "units wherein" should read --units, wherein--.

At column 30, line 28 "corresponding" should read --correspond--.

At column 30, lines 38-39 "carbanions C1-C20" should read --carbanions, C1-C20--.

At column 30, line 41 "C114 C20" should read --C1-C20--.

At column 30, line 42 "thereof, W" should read --thereof; W--.

At column 30, line 43 "is hydrophobic" should read --is a hydrophobic--.

At column 30, line 55 "thereof, and" should read --thereof; and--.

At column 31, line 17 "1, wherein" should read --1 wherein--.

At column 31, line 20 "poly(4-t-butylstyrene)" should read --Poly (poly(4-t-butylstyrene)

Signed and Sealed this

Tenth Day of February, 1998

*Attest:*

BRUCE LEHMAN

*Attesting Officer*   Commissioner of Patents and Trademarks